United States Patent
Wong et al.

(10) Patent No.: US 10,124,032 B2
(45) Date of Patent: Nov. 13, 2018

(54) SEVEN-STAR TEA WITHOUT EXCIPIENT AND METHOD OF PREPARING THE SAME

(71) Applicant: Eu Yan Sang International Ltd, Singapore (SG)

(72) Inventors: Suet Ying Wong, Hong Kong (CN); Kim Wu, Hong Kong (CN); Kuen Kuen Ella Lee, Hong Kong (CN)

(73) Assignee: Eu Yan Sang International Ltd, Singapore (SG)

( * ) Notice: Subject to any disclaimer, the term of this patent is extended or adjusted under 35 U.S.C. 154(b) by 864 days.

(21) Appl. No.: 14/412,485

(22) PCT Filed: Jul. 2, 2013

(86) PCT No.: PCT/SG2013/000274
§ 371 (c)(1),
(2) Date: Jan. 2, 2015

(87) PCT Pub. No.: WO2014/007760
PCT Pub. Date: Jan. 9, 2014

(65) Prior Publication Data
US 2015/0164971 A1    Jun. 18, 2015

(30) Foreign Application Priority Data
Jul. 3, 2012  (CN) .......................... 2012 1 0229521

(51) Int. Cl.
| | | |
|---|---|---|
| *A61K 36/00* | (2006.01) | |
| *A61K 36/8994* | (2006.01) | |
| *A23F 3/34* | (2006.01) | |
| *A61K 35/64* | (2015.01) | |
| *A61K 36/36* | (2006.01) | |
| *A61K 36/48* | (2006.01) | |
| *A61K 36/484* | (2006.01) | |
| *A61K 36/734* | (2006.01) | |
| *A61K 36/74* | (2006.01) | |
| *A61K 36/88* | (2006.01) | |
| *A23L 33/105* | (2016.01) | |
| *A61K 35/63* | (2015.01) | |

(52) U.S. Cl.
CPC ............ *A61K 36/8994* (2013.01); *A23F 3/34* (2013.01); *A23L 33/105* (2016.08); *A61K 35/63* (2015.01); *A61K 35/64* (2013.01); *A61K 36/00* (2013.01); *A61K 36/36* (2013.01); *A61K 36/48* (2013.01); *A61K 36/484* (2013.01); *A61K 36/734* (2013.01); *A61K 36/74* (2013.01); *A61K 36/88* (2013.01)

(58) Field of Classification Search
None
See application file for complete search history.

(56) References Cited

FOREIGN PATENT DOCUMENTS

| | | |
|---|---|---|
| CN | 1189971 | 8/1998 |
| CN | 1701671 | 11/2005 |
| CN | 100998795 | 7/2007 |
| TW | 201225860 | 7/2012 |
| WO | WO 2012/088794 | 7/2012 |

OTHER PUBLICATIONS

International Search Report and Written Opinion in International Application No. PCT/SG2013/000274, dated Apr. 10, 2013, 10 pages.
"Seven star tea for children," Learn Chinese Recipe, http://learnchineserecipe.com/1163/chinese-recipe/seven-star-tea-for-children, retrieved on Apr. 9, 2015, May 25, 2012, 2 pages.

*Primary Examiner* — Terry A McKelvey
*Assistant Examiner* — Catheryne Chen
(74) *Attorney, Agent, or Firm* — Fish & Richardson P.C.

(57) ABSTRACT

The present invention relates to a seven-star tea without excipient comprising Coicis Semen, Oryzae Fructus Germinatus, *Triticum Aestivum*, Herba Lophatheri, Fructus Crataegi, Ramulus Uncariae Cum Uncis, Periostracum Cicadae and Radix Et Rhizoma Glycyrrhizae, wherein the *Triticum Aestivum* is used as a forming agent in the seven-star tea, and methods for the preparation thereof. The seven-star tea of the present invention is specially suitable for children, since it has the effects of promoting appetite and removing food stagnation, clearing heat and arresting convulsion, and long-term intake of sucrose or other excipients which are not beneficial for their health is avoided.

13 Claims, No Drawings

SEVEN-STAR TEA WITHOUT EXCIPIENT AND METHOD OF PREPARING THE SAME

CROSS-REFERENCE TO RELATED APPLICATIONS

This application is a National Stage application under 35 U.S.C. § 371 of International Application No. PCT/SG2013/000274, having and International Filing Date of Jul. 2, 2013, which claims priority to Chinese Application No. 201210229521.5, filed on Jul. 3, 2012. The disclosure of the prior applications are considered part of and are incorporated by reference in the disclosure of this application.

FIELD OF THE INVENTION

The present invention relates to a seven-star tea and a method of preparing the same, and particularly relates to a seven-star tea without excipient and a method of preparing the same.

BACKGROUND OF THE INVENTION

Seven-star tea mainly aims at intestine heat and stomach heat resulted from children's long-term intake of milk product. Accordingly, seven-star tea is usually used to relieve the intestine heat and stomach heat caused by children's intake of milk product.

Presently, two main types of seven-star tea are available in the market. One type of seven-star tea is in the form of traditional pack in which different raw materials of the formula of seven-star tea are directly packed. This type of seven-star tea requires users to decoct and concoct the different raw materials in person, which needs a long preparation time and results in different drug properties, even makes drug effects to vary greatly because of differences in the process of decoction or concoction. Another type of seven-star tea is in the form of ready-for-use granules, such products mostly contain excipients. It is generally thought that excipients are inactive ingredients and mainly used to assist drugs to give form or for disintegration, dissolving purposes during intake. Typically, starch, lactose, sucrose and the like are used as excipients in drugs. However, starch is a kind of water-insoluble excipient which cannot be dissolved in water, it is therefore not suitable to be used as excipient in completely soluble granules. Moreover, it has great impact to children's health to take in lactose, sucrose or other additives for a long time. For example, excessive intake of them will cause tooth decay, and long-term intake of them will cause obesity. In addition, blood sugar level of diabetic patients will rise due to long-term intake of sucrose.

Therefore, in order to overcome the above-mentioned deficiencies existing in the prior art, there is a need to develop a ready-for-use seven-star tea without excipient.

SUMMARY OF THE INVENTION

One objective of the present invention is to provide a ready-for-use seven-star tea without excipient.

In order to realize the above objective, the present invention provides a technical solution as follows: a seven-star tea without excipient comprises the following medicinal materials: Coicis Semen, Oryzae Fructus Germinatus, *Triticum Aestivum*, Herba Lophatheri, Fructus Crataegi, Ramulus Uncariae Cum Uncis, Periostracum Cicadae and Radix Et Rhizoma Glycyrrhizae, wherein the *Triticum Aestivum* is used as a forming agent in the seven-star tea.

In the seven-star tea without excipient according to the present invention, the weight percentages of the above medicinal materials are preferably as follows: 15-30% of Coicis Semen, 15-30% of Oryzae Fructus Germinatus, 15-25% of *Triticum Aestivum*, 10-20% of Herba Lophatheri, 5-15% of Fructus Crataegi, 5-10% of Ramulus Uncariae Cum Uncis, 1-8% of Periostracum Cicadae, and 1-8% of Radix Et Rhizoma Glycyrrhizae, based on the total weight of the medicinal materials constituting the seven-star tea at 100%.

According to a further preferred embodiment of the present invention, the weight percentages of the medicinal materials are as follows: 18-25% of Coicis Semen, 18-25% of Oryzae Fructus Germinatus, 18-22% of *Triticum Aestivum*, 12-18% of Herba Lophatheri, 8-12% of Fructus Crataegi, 6-8% of Ramulus Uncariae Cum Uncis, 2-5% of Periostracum Cicadae, and 2-5% of Radix Et Rhizoma Glycyrrhizae, based on the total weight of the medicinal materials constituting the seven-star tea at 100%.

According to a furthermore preferred embodiment of the present invention, the weight percentages of the medicinal materials are as follows: 20.64% of Coicis Semen, 20.64% of Oryzae Fructus Germinatus, 20.00% of *Triticum Aestivum*, 15.49% of Herba Lophatheri, 10.31% of Fructus Crataegi, 7.74% of Ramulus Uncariae Cum Uncis, 2.59% of Periostracum Cicadae, and 2.59% of Radix Et Rhizoma Glycyrrhizae, based on the total weight of the medicinal materials constituting the seven-star tea at 100%.

In addition, it should be noted that in the seven-star tea without excipient provided in the present invention, based on the above basic formula, the above basic formula can be adjusted by adding other medicinal materials to meet various demands of customers. For example, the addition of Pseudostellariae Radix can strengthen the effect of invigorating spleen and replenishing qi, and the effect of moistening lung and promoting production of body fluids; the addition of Radix Ophiopogonis can strengthen the effect of nourishing yin and promoting production of fluid, and the effect of moistening lung and promoting production of body fluids; the addition of Semen Lablab Album can strengthen the effect of invigorating spleen for eliminating dampness, and the effect of regulating stomach and relieving summer heat. Similarly, a skilled person in the art can add other different medicinal materials into the basic formula of seven-star tea as required. Furthermore, it will be appreciated by those skilled in the art that such modification based on the basic formula of seven-star tea should fall into the scope of the present invention as defined by the appended claims.

In addition, the present invention further provides a method of preparing the seven-star tea without excipient, which comprises the following steps:

(a) weighing the medicinal materials according to the formula of seven-star tea;

(b) mixing the medicinal materials except for *Triticum Aestivum* together, decocting the resulting mixture with water 1-3 time(s), each time lasting for 0.5-2 hours, then combining the decoctions obtained from each time, filtering, and concentrating the resulting filtrate into a concentrated solution with relative density of 1.0-1.3 g/cm$^3$;

(c) pulverizing the weighed *Triticum Aestivum* into particles of 15-40 mesh size, then dispersing the concentrated solution obtained from the step (b) to the pulverized particles of *Triticum Aestivum*;

(d) fully drying the pulverized particles of *Triticum Aestivum* loaded with the concentrated solution obtained from the step (c), then packing the particles in a desired product form.

In the method of preparing the seven-star tea without excipient according to the present invention, the step (b) preferably comprises the following steps: mixing seven medicinal materials, namely Coicis Semen, Oryzae Fructus Germinatus, Herba Lophatheri, Fructus Crataegi, Ramulus Uncariae Cum Uncis, Periostracum Cicadae and Radix Et Rhizoma Glycyrrhizae or more, decocting the resulting mixture with water 2 times, each time lasting for 1 hour, then combining the decoctions obtained from each time, filtering, and concentrating the resulting filtrate into a concentrated solution with relative density of 1.1-1.2 g/cm³ which is determined at 45-50° C.

In the method of preparing the seven-star tea without excipient according to the present invention, the step (c) preferably comprises the following steps: pulverizing the weighed *Triticum Aestivum* into particles of 25-35 mesh size, then spraying the concentrated solution obtained from step (b) to the pulverized particles of *Triticum Aestivum* by utilizing flow layer drying equipment; further preferably, the weighed *Triticum Aestivum* is pulverized into particles of about 30 mesh size in the step (c).

In the method of preparing the seven-star tea without excipient according to the present invention, the step (d) preferably comprises the step of packing the particles in tea bags.

In addition, it should be noted that, when the seven-star tea comprises other medicinal materials besides those of the basic formula, effective ingredients can be extracted from the other medicinal materials by using conventional methods in the field of Chinese medicinal preparations according to the characteristics of the medicinal materials; alternatively, the other medicinal materials can be mixed with those of the basic formula, and the resulting mixture is decocted with proper amount of water, then the seven-star tea can be prepared according to the method of the present invention mentioned above.

Compared with the prior seven-star tea, the seven-star tea according to the present invention has the following advantageous effects:

The technical solution of the present invention is a breakthrough of conventional formula and preparation method of seven-star tea in the prior art. *Triticum Aestivum*, a raw medicinal material, is used as the forming agent, and at the same time it is used as one of the raw materials of the seven-star tea which has an effect of removing deficient heat. The main reason for replacing conventional excipients with *Triticum Aestivum* is that *Triticum Aestivum* can absorb an extracted solution more easily than other raw materials. When the effective ingredients extracted from other raw materials are sprayed into the pulverized particles of *Triticum Aestivum* and the resulting particles loaded with the effective ingredients are packed in tea bags, the concentrated solution can be released immediately and all active ingredients can fully diffuse into water when the seven-star tea is mixed and consumed with boiled water. Since solid residue will not be released in water, compared to the direct use of raw medicinal materials packed in tea bags, the effective ingredients of the seven-star tea of the present invention can be released more easily. Furthermore, due to the use of very mature preparing technology and equipments in the field of Chinese medicinal preparations, the method of the present invention has proved easy to perform with high production efficiency.

Because the present invention provides the above formula and preparation method, users can avoid long-term intake of excipients or other unnecessary components. Particularly, the seven-star tea of the present invention is specially suitable for children who have trouble with intestine heat and stomach heat resulted from their long-term intake of milk product, since long-term intake of unnecessary components such as sucrose or other excipients which are not beneficial for their health is avoided. Moreover, the seven-star tea of the present invention is also suitable for diabetic patients.

Since the concentrated solution containing active ingredients is absorbed into the pulverized particles of *Triticum Aestivum*, the concentrated solution can be released immediately and the active ingredients can fully diffuse in water once they contact with water during the process of consumption. Therefore, the seven-star tea of the present invention can even be taken after being mixed with warm boiled water. Moreover, the seven-star tea of the present invention has a characteristic of low dosage but highly effective.

DETAILED DESCRIPTION OF PREFERRED EMBODIMENTS

The seven-star tea without excipient and the method of preparing the same according to the present invention will be described in detail by the following embodiments. It should be understood, however, that the invention is not limited to the following embodiments, and the invention may be varied in other manner so as to not depart from the spirit and scope of the invention.

EXAMPLES

Example 1

The medicinal materials of seven-star tea of the present invention are weighed according to the following weight percentages: 20.64% of Coicis Semen, 20.64% of Oryzae Fructus Germinatus, 20.00% of *Triticum Aestivum*, 15.49% of Herba Lophatheri, 10.31% of Fructus Crataegi, 7.74% of Ramulus Uncariae Cum Uncis, 2.59% of Periostracum Cicadae, and 2.59% of Radix Et Rhizoma Glycyrrhizae. The total weight of the above eight medicinal materials is 100 g. Seven medicinal materials, namely Coicis Semen, Oryzae Fructus Germinatus, Fructus Crataegi, Herba Lophatheri, Ramulus Uncariae Cum Uncis, Periostracum Cicadae and Radix Et Rhizoma Glycyrrhizae are mixed together. The resulting mixture is decocted with water 2 times, and each decocting time lasts for 1 hour, then the decoctions obtained from each time are combined and filtered. Thereafter, the resulting filtrate is concentrated into a concentrated solution with relative density of about 1.1 g/cm³ (45-50° C.) and the weight of the concentrated solution is 40 g by utilizing flow layer drying equipment. The weighed *Triticum Aestivum* is pulverized into particles of about 30 mesh size, and the concentrated solution obtained is sprayed into the pulverized particles of *Triticum Aestivum*. The pulverized particles of *Triticum Aestivum* loaded with the concentrated solution are fully dried into 30 g of final product, which is packed in tea bags of 2 grams/bag and 10 bags/box.

Example 2

The medicinal materials of seven-star tea of the present invention are weighed according to the following weight percentages: 18.76% of Coicis Semen, 18.18% of Oryzae Fructus Germinatus, 18.76% of *Triticum Aestivum*, 14.08% of Herba Lophatheri, 9.37% of Fructus Crataegi, 7.04% of Ramulus Uncariae Cum Uncis, 2.35% of Periostracum Cicadae, 2.35% of Radix Et Rhizoma Glycyrrhizae and 9.09%

Pseudostellariae Radix. The total weight of the above nine medicinal materials is 100 g. The above eight medicinal materials except for *Triticum Aestivum* are mixed together. The resulting mixture is decocted with water 2 times, and each decocting time lasts for 1 hour, then the decoctions obtained from each time are combined and filtered. Thereafter, the resulting filtrate is concentrated into a concentrated solution with relative density of about 1.1 g/cm$^3$ (45-50° C.) and the weight of the concentrated solution is 40 g by utilizing flow layer drying equipment. The weighed *Triticum Aestivum* is pulverized into particles of about 30 mesh size, and the concentrated solution obtained is sprayed into the pulverized particles of *Triticum Aestivum*. The pulverized particles of *Triticum Aestivum* loaded with the concentrated solution are fully dried into 30 g of final product, which is packed in tea bags of 2 grams/bag and 10 bags/box.

In this example, Pseudostellariae Radix is added into the basic formula of seven-star tea of the present invention. Therefore, the seven-star tea prepared in this example not only has the essential functions described above, but also can strengthen the effect of invigorating spleen and replenishing qi, and the effect of promoting production of fluid and moistening lung.

Example 3

The medicinal materials of seven-star tea of the present invention are weighed according to the following weight percentages: 18.76% of Coicis Semen, 18.18% of Oryzae Fructus Germinatus, 18.76% of *Triticum Aestivum*, 14.08% of Herba Lophatheri, 9.37% of Fructus Crataegi, 7.04% of Ramulus Uncariae Cum Uncis, 2.35% of Periostracum Cicadae, 2.35% of Radix Et Rhizoma Glycyrrhizae and 9.09% of Radix Ophiopogonis. The total weight of the above nine medicinal materials is 100 g. The above eight medicinal materials except for *Triticum Aestivum* are mixed together. The resulting mixture is decocted with water 2 times, and each decocting time lasts for 1.5 hours, then the decoctions obtained from each time are combined and filtered. Thereafter, the resulting filtrate is concentrated into a concentrated solution with relative density of about 1.2 g/cm$^3$ (45-50° C.) and the weight of the concentrated solution is 40 g by utilizing flow layer drying equipment. The weighed *Triticum Aestivum* is pulverized into particles of about 30 mesh size, and the concentrated solution obtained is sprayed into the pulverized particles of *Triticum Aestivum*. The pulverized particles of *Triticum Aestivum* loaded with the concentrated solution are fully dried into 30 g of final product, which is packed in tea bags of 2 grams/bag and 10 bags/box.

In this example, Radix Ophiopogonis is added into the basic formula of seven-star tea of the present invention. Therefore, the seven-star tea prepared in this example not only has the essential functions described in the invention, but also can strengthen the effect of nourishing yin for promoting production of fluid, and the effect of moistening lung and promoting production of fluid.

Example 4

The medicinal materials of seven-star tea of the present invention are weighed according to the following weight percentages: 18.76% of Coicis Semen, 18.18% of Oryzae Fructus Germinatus, 18.76% of *Triticum Aestivum*, 14.08% of Herba Lophatheri, 9.37% of Fructus Crataegi, 7.04% of Ramulus Uncariae Cum Uncis, 2.35% of Periostracum Cicadae, 2.35% of Radix Et Rhizoma Glycynhizae and 9.09% of Semen Lablab Album. The total weight of the above nine medicinal materials is 100 g. The above eight medicinal materials except for *Triticum Aestivum* are mixed together. The resulting mixture is decocted with water 3 times, and each decocting time lasts for 0.8 hour, then the decoctions obtained from each time are combined and filtered. Thereafter, the resulting filtrate is concentrated into a concentrated solution with relative density of about 1.2 g/cm$^3$ (45-50° C.) and the weight of the concentrated solution is 40 g by utilizing flow layer drying equipment. The weighed *Triticum Aestivum* is pulverized into particles of about 30 mesh size, and the concentrated solution obtained is sprayed into the pulverized particles of *Triticum Aestivum*. The pulverized particles of *Triticum Aestivum* loaded with the concentrated solution are fully dried into 30 g of final product, which is packed in tea bags of 2 grams/bag and 10 bags/box.

In this example, Semen Lablab Album is added into the basic formula of seven-star tea of the present invention. Therefore, the seven-star tea prepared in this example not only has the essential functions described in the invention, but also can strengthen the effect of invigorating spleen for eliminating dampness, and the effect of regulating stomach and clearing summer heat.

The invention claimed is:

1. A method of preparing a seven-star tea without excipient comprising the following materials: Coicis Semen, Oryzae Fructus Germinatus, *Triticum Aestivum*, Herba Lophatheri, Fructus Crataegi, Ramulus Uncariae Cum Uncis, Periostracum Cicadae and Radix Et Rhizoma Glycyrrhizae, wherein the method comprises:
   (a) weighing the medicinal materials wherein the weight percentages are as follows: 15-30% of Coicis Semen, 15-30% of Oryzae Fructus Germinatus, 15-25% of *Triticum Aestivum*, 10-20% of Herba Lophatheri, 5-15% of Fructus Crataegi, 5-10% of Ramulus Uncariae Cum Uncis, 1-8% of Periostracum Cicadae and 1-8% of Radix Et Rhizoma Glycyrrhizae, based on the total weight of the medicinal materials;
   (b) mixing the medicinal materials except for *Triticum Aestivum* together, and decocting the resulting mixture with water 1-3 time(s), wherein each decocting step lasts for 0.5-2 hours;
   (c) combining the decoctions obtained from step (b), filtering, and concentrating the resulting filtrate into a concentrated solution with relative density of 1.0-1.3 g/cm$^3$;
   (d) pulverizing the weighed *Triticum Aestivum* into particles of 15-40 (~1060-371 μm) mesh size, and then dispersing the concentrated solution obtained from the step (c) to the pulverized particles of *Triticum Aestivum*; and
   (e) fully drying the pulverized particles of *Triticum Aestivum* loaded with the concentrated solution obtained from the step (d), then packing the particles in a desired product form.

2. The method according to claim 1, wherein the method comprises
   (b) mixing the other medicinal materials except for *Triticum Aestivum* together, and decocting the resulting mixture with water 2 times, wherein each decocting step lasts for 1 hour; and
   (c) combining the decoctions obtained from step (b), filtering, and concentrating the resulting filtrate into a concentrated solution with relative density of 1.1-1.2 g/cm$^3$.

3. The method according to claim 2, wherein the step (d) comprises:

pulverizing the weighed *Triticum Aestivum* into particles of 25-35 (~593-424 μm) mesh size, and then spraying the concentrated solution obtained from step (c) to the pulverized particles of *Triticum Aestivum* by utilizing flow layer drying equipment.

4. The method of according to claim 3, wherein the *Triticum Aestivum* is pulverized into about 30 (~494 μm) mesh size in the step (d).

5. The method according to claim 4, wherein the pulverized *Triticum Aestivum* is packed in tea bags in the step (e).

6. The method according to claim 1, wherein the weight percentages of the medicinal materials are as follows: 18-25% of Coicis Semen, 18-25% of Oryzae Fructus Germinatus, 18-22% of *Triticum Aestivum*, 12-18% of Herba Lophatheri, 8-12% of Fructus Crataegi, 6-8% of Ramulus Uncariae Cum Uncis, 2-5% of Periostracum Cicadae and 2-5% of Radix Et Rhizoma Glycyrrhizae, based on the total weight of the medicinal materials.

7. The method according to claim 1, wherein the weight percentages of the medicinal materials are as follows: 20.64% of Coicis Semen, 20.64% of Oryzae Fructus Germinatus, 20.00% of *Triticum Aestivum*, 15.49% of Herba Lophatheri, 10.31% of Fructus Crataegi, 7.74% of Ramulus Uncariae Cum Uncis, 2.59% of Periostracum Cicadae and 2.59% of Radix Et Rhizoma Glycyrrhizae, based on the total weight of the medicinal materials.

8. The method according to claim 1 , wherein the seven-star the further comprises Pseudostellariae Radix.

9. The method according to claim 8, wherein the weight percentages of the medicinal materials are as follows: 18.76% of Coicis Semen, 18.18% of Oryzae Fructus Germinatus, 18.76% of *Triticum Aestivum*, 14.08% of Herba Lophatheri, 9.37% of Fructus Crataegi, 7.04% of Ramulus Uncariae Cum Uncis, 2.35% of Periostracum Cicadae, 2.35% of Radix Et Rhizoma Glycyrrhizae and 9.09% Pseudostellariae Radix.

10. The method according to claim 1, wherein the seven-star tea further comprises Radix Ophiopogonis.

11. The method according to claim 10, wherein the weight percentages of the medicinal materials are as follows: 18.76% of Coicis Semen, 18.18% of Oryzae Fructus Germinatus, 18.76% of *Triticum Aestivum*, 14.08% of Herba Lophatheri, 9.37% of Fructus Crataegi, 7.04% of Ramulus Uncariae Cum Uncis, 2.35% of Periostracum Cicadae, 2.35% of Radix Et Rhizoma Glycyrrhizae and 9.09% of Radix Ophiopogonis.

12. The method according to claim 1, wherein the seven-star tea further comprises Semen Lablab Album.

13. The method according to claim 12, wherein the weight percentages of the medicinal materials are as follows: 18.76% of Coicis Semen, 18.18% of Oryzae Fructus Germinatus, 18.76% of *Triticum Aestivum*, 14.08% of Herba Lophatheri, 9.37% of Fructus Crataegi, 7.04% of Ramulus Uncariae Cum Uncis, 2.35% of Periostracum Cicadae, 2.35% of Radix Et Rhizoma Glycyrrhizae and 9.09% of Semen Lablab Album.

* * * * *

UNITED STATES PATENT AND TRADEMARK OFFICE
CERTIFICATE OF CORRECTION

PATENT NO. : 10,124,032 B2
APPLICATION NO. : 14/412485
DATED : November 13, 2018
INVENTOR(S) : Suet Ying Wong, Kim Wu and Kuen Kuen Ella Lee Page 1 of 1

It is certified that error appears in the above-identified patent and that said Letters Patent is hereby corrected as shown below:

In the Claims

Column 7, Line 6, Claim 4, after "method" delete "of".

Signed and Sealed this
Third Day of November, 2020

Andrei Iancu
*Director of the United States Patent and Trademark Office*